United States Patent
Blomberg et al.

(10) Patent No.: US 10,001,409 B2
(45) Date of Patent: Jun. 19, 2018

(54) INFRARED EMITTER HAVING A LAYERED STRUCTURE

(71) Applicant: TEKNOLOGIAN TUTKIMUSKESKUS VTT OY, Espoo (FI)

(72) Inventors: Martti Blomberg, Espoo (FI); Hannu Kattellus, Espoo (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 0 days. days.

(21) Appl. No.: 15/720,079

(22) Filed: Sep. 29, 2017

(65) Prior Publication Data

US 2018/0120158 A1 May 3, 2018

(30) Foreign Application Priority Data

Oct. 28, 2016 (FI) ..................... 20165816

(51) Int. Cl.
*G01N 21/35* (2014.01)
*G01J 3/10* (2006.01)

(52) U.S. Cl.
CPC .............. *G01J 3/108* (2013.01); *G01N 21/35* (2013.01)

(58) Field of Classification Search
CPC ................................ G01J 3/108; G01N 21/35
USPC ......... 250/493.1, 494.1, 495.1, 503.1, 504 R
See application file for complete search history.

(56) References Cited

U.S. PATENT DOCUMENTS

| 2012/0267532 A1 | 10/2012 | Udrea et al. |
| 2015/0123016 A1 | 5/2015 | Nagatani et al. |
| 2015/0241612 A1 | 8/2015 | Talvitie et al. |

FOREIGN PATENT DOCUMENTS

| EP | 0776023 B1 | 10/2001 |
| WO | 02080620 A1 | 10/2002 |

OTHER PUBLICATIONS

Feb. 20, 2017 Office Action issued in Finnish Patent Application No. 20165816.
Feb. 20, 2017 Search Report issued in Finnish Patent Application No. 20165816.
Laamanen, M. et al., "Thin film absorbers for visible, near-infrared, and short-wavelength infrared spectra," Procedia Chemistry, vol. 1, 2009, pp. 393-396.
Liddiard, K.C., "Application of Interferometric Enhancement to Self-Absorbing Thin Film Thermal IR Detectors," 1993, Infrared Phys., vol. 34, No. 4, pp. 379-387.

*Primary Examiner* — Nicole Ippolito
*Assistant Examiner* — Hanway Chang
(74) *Attorney, Agent, or Firm* — Oliff PLC

(57) ABSTRACT

A layered infrared emitter structure includes only semi-transparent metal layers, preferably one semi-transparent metal layer, and one or more dielectric layers on both sides of the semi-transparent metal layer. Further, an electric heating wiring is arranged in or between any of the dielectric layers to heat the semi-transparent metal layer up to a required infrared emission temperature, preferably to a temperature within a range from 400° C. to 1000° C.

13 Claims, 6 Drawing Sheets

| 10 | SI3N4 | 100 nm |
| 11 | SIPOLY | 175 nm |
| 12 | SI3N4 | 30 nm |
| 13 | Al2O3 | 10 nm |
| 14 | Nb | 11 nm |
| 15 | Al2O3 | 10 nm |
| 16 | SI3N4 | 150 nm |

INFRARED EMITTER HAVING A LAYERED STRUCTURE

FIELD OF THE INVENTION

The present invention relates to optical infrared emitters having a layered structure

BACKGROUND OF THE INVENTION

Optical spectrometers are widely used when the composition of a gas or a fluid must be measured. Such measurements are needed in industry, science, medicine, pharmacy, agriculture and biology in a wide range of applications. Infrared emitters play an important role in the development of highly accurate chemical sensors, and serve as the principal infrared emitting element in optical gas sensor systems. Conventionally an IR (infrared) emitter has taken the form of a wire, filament or conductive ceramic element heated by electrical current. The infrared emission is dependent on temperature and area of the heated surface. The demand for small-sized spectrometers for portable measuring devices and system integrated sensors has resulted in increasing interest in microspectrometers. Some commercial solutions are based on simple thin film emitters of, for example, tungsten or platinum. However, emissivity of tungsten or platinum is low.

Optically black surfaces can be used either as an absorber or an emitter. Absorbers are needed in thermal detectors and emitters in thermal infrared sources. The former do not need to withstand as high temperatures as the latter.

Emissivity of a simple metal surface can be enhanced multifold by adding properly tailored thin film layer structure on top of the metal. In order to be able to use the optical structure as an emitter, the structure must withstand the temperature required in emitter use. Typically, in emitter applications temperatures of more than 100° C. are used, which the structure should preferably withstand unchanged for even long periods of time. The operating temperature can also be higher, for example at least 200° C., at least 300° C., or even more than 650° C. Emitter temperatures most usually used are in the range 100-1000° C., for example in the range 200-650° C., such as in the range 250-400° C. Thus, the structure should withstand the design temperature for the application and remain stable in the selected operating temperature range for very long periods of time. At the same time, the structure should permit a good optical matching. Stability means that the emissivity of the structure remains essentially unchanged at the desired wavelength range in the operating conditions of the structure for the duration of the operating life of the structure.

Manufacturing of the layered structure suitable for emitter use is, therefore, very demanding, because the effective emitter use of the component requires a high temperature. For this reason, most of the known absorber structures are not in practice suitable for emitter use.

Absorber structure presented by Liddiard K.C. (Infrared Physics, 1993, vol. 34, 4, pp. 379) cannot be used as infrared emitter because it will not tolerate the temperatures demanded in emitter use. In Liddiard's solution a thin semi-transparent metal layer and a dielectric layer are on top of non-transparent metal layer. The thin metal layer together with the dielectric layer forms an antireflective layer structure so that reflection from the surface is very low at desired wavelength range. Thus with low reflection and zero transmission, high absorption efficiency can be obtained.

U.S. Pat. No. 6,177,673 discloses an infrared absorber which is based on use of doped silicon and non-transparent metal layer. This kind of structure is not optically stable in emitter use. The main reason for the optical instability is the activation level of dopants (solid solubility) that is dependent on temperature.

US2015241612 discloses an infrared emitter structure which is based on the same operating principle as the Liddiard's absorber. A thin metal layer and an underlying dielectric layer are used as antireflective layers on top of a non-transparent reflective metal layer. Optical stability is achieved by protecting the thin lossy metal layer with one or more shielding layers.

The article "Thin film absorbers for visible, near-infrared, and short-wavelength infrared spectra", Proceedings of the Eurosensors XXIII conference, Procedia Chemistry Volume 1, Issue 1, September 2009, Pages 393-396, discloses an absorber structure which is basically the same structure as the emitter structure presented in US 2015241612.

Stable light sources with high emission efficiency are not available in the market. Present commercial solutions are expensive, and either of low efficiency and large power consumption, or not sold as discrete light-emitting devices.

There is a need for low cost, low power consumption, stable infrared source, especially for spectroscopic and NDIR gas, liquid and solid matter measurement applications.

BRIEF DESCRIPTION OF THE INVENTION

An aspect of the invention is a layered infrared emitter structure with reduced thermal mass and thermal conductivity.

Another aspect of the invention is a layered infrared emitter structure with reduced manufacturing cost.

An aspect of the invention is an infrared emitter device as recited in the independent claim 1. The preferred embodiments of the invention are disclosed in the dependent claims.

An aspect of the invention is a layered infrared emitter device, which comprises a layered structure having at least one metal layer stacked between two or more dielectric layers, and an electric heating means arranged in or between any of the dielectric layers to heat the at least one metal layer to a required infrared emission temperature, preferably to a temperature within a range from 400° C. to 1000° C., wherein each metal layer in the layered structure is a semi-transparent metal layer.

In an embodiment, the layered structure comprises only one metal layer, and wherein the only one metal layer is a semi-transparent metal layer.

In an embodiment, the layered structure comprises a stack of semi-transparent metal layers.

In an embodiment, the thickness of the semi-transparent metal layer is selected from a range 2 nm to 50 nm, preferably from a range 3 nm to 20 nm, more preferably from a range 5 nm to 15 nm.

In an embodiment, the semi-transparent metal layer is made of a thermally stable metal, the metal being preferably selected from preferably selected from refractory or noble metals, more preferably from the group of such as molybdenum, tungsten, titanium, tantalum, palladium, platinum or niobium.

In an embodiment, at least one of the dielectric layers is adapted to optically match the at least one semi-transparent metal layer to an emitting outer surface of the layered structure, and wherein the at least one optically-matching dielectric layer is being preferably made of polysilicon material or other dielectric material having a high refractive index.

In an embodiment, the at least one optically-matching dielectric layer is located between the at least one semi-transparent metal layer and the emitting outer surface of the layered structure.

In an embodiment, the thickness of the at least one optically-matching dielectric layer is several times larger than the thickness of the at least one semi-transparent metal layer.

In an embodiment, the at least one optically-matching dielectric layer and/or the at least one semi-transparent metal layer is patterned, partly patterned or non-patterned.

In an embodiment, the dielectric layers include shielding layers adapted to enclose the at least one semi-transparent layer to prevent chemical reactions with other layers of the layered structure as well as with ambient agents.

In an embodiment, the dielectric layers include shielding layers adapted to prevent chemical reactions between different layers of the layered structure as well as with ambient agents, at least one of the shielding layers being preferably made of material selected from a group of silicon nitrate, polycrystalline, and metal oxides, such as aluminium oxide.

In an embodiment, the layered structure comprises in order from an emitting side to an opposite side,
at least one shielding dielectric layer,
an optically-matching dielectric layer having a high refractive index,
at least one shielding dielectric layer,
the semi-transparent metal layer,
at least one shielding dielectric layer,
and wherein the electric heating means is arranged in or between of the shielding dielectric layers.

In an embodiment, the layered structure comprises in order from an emitting side to an opposite side
a first shielding dielectric layer,
an optically-matching dielectric layer having a high refractive index,
a second shielding dielectric layer,
a third shielding dielectric layer,
the semi-transparent metal layer which is the only metal layer in the layered structure,
a fourth shielding dielectric layer, and
a fifth shielding dielectric layer, and
the electric heating means being arranged in or between any one of the shielding dielectric layers.

A further aspect of the invention is use of an infrared emitter device according any embodiment or combination of embodiments for spectroscopic or NDIR gas, liquid or solid matter measurement.

BRIEF DESCRIPTION OF THE DRAWINGS

In the following the invention will be described in greater detail by means of exemplary embodiments with reference to the attached drawings, in which.

EXEMPLARY EMBODIMENTS OF THE INVENTION

Figure 1A:
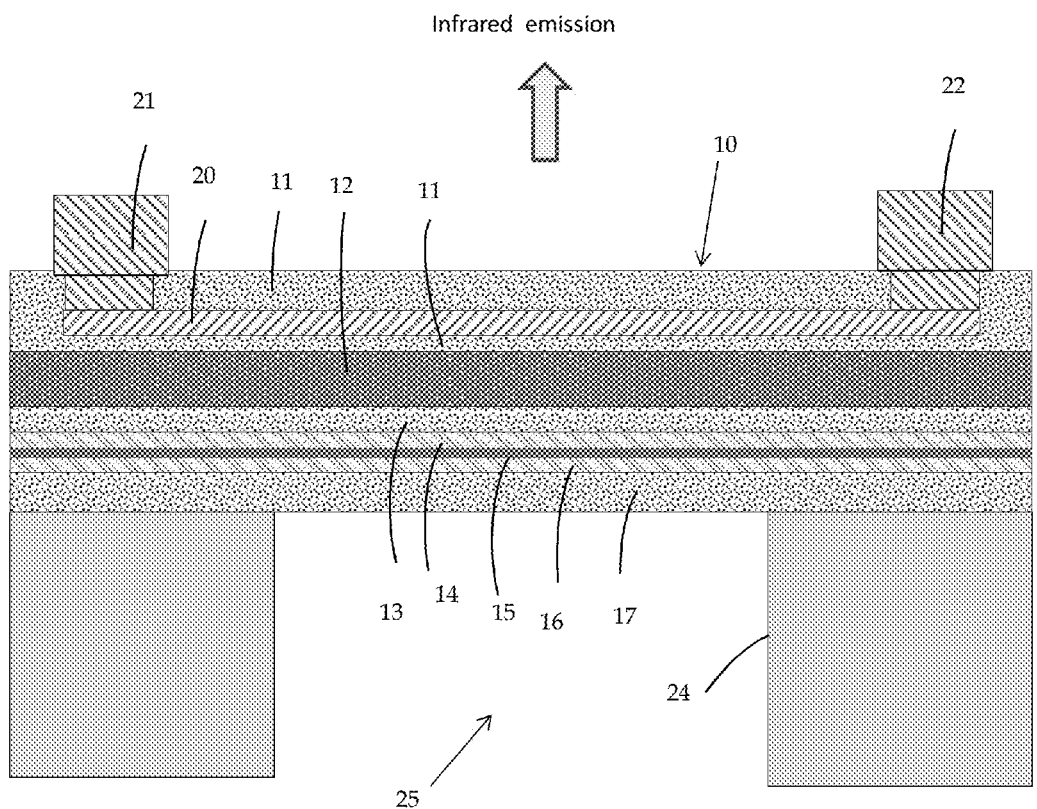
FIG. 1A shows a cross-sectional side view of a layered infrared emitter device according to an exemplary embodiment of the invention.

An aspect of the invention is a layered infrared emitter structure which includes only semi-transparent metal layers, preferably one semi-transparent metal layer, and one or more dielectric layers on both sides of the semi-transparent metal layer. Semi-transparent metal absorbs one part of the radiant energy and the other part of the radiant energy passes through the material. In addition, a third part of the radiant energy can be reflected from the surface of the semi-transparent metal. Thus, a semi-transparent metal is a lossy material. Furthermore, an electric heating wiring is arranged in or between any of the dielectric layers to heat the semi-transparent metal layer or layers up to a required infrared emission temperature, preferably to a temperature within a range from 400° C. to 1000° C. The stack of dielectric layers together with semi-transparent lossy material can be optically matched for maximum emission. Emissivity expresses the energy radiated by the surface relative to the energy radiated by a black body at the same temperature. The dielectric layers can also be so called protecting or shielding layers if they prevent chemical reactions between layers inside the stack or chemical reactions of layers with the ambient gas.

In the conventional layered infrared absorber and emitter structures, such as that disclosed in US201524161, there is a thick non-transparent reflective metal layer at the bottom of the stack. In the layered structure according to the invention, the thick non-transparent reflective metal layer is avoided. This results in lower thermal mass, and in faster operation. The layered structure of embodiments of the invention can be made thinner than the conventional structures, which results in lower thermal losses and thermal conductivity, and thus low power consumption is possible. There can also be a lower number of patterned layers in embodiments of the present invention, and the manufacturing process can be simpler and the manufacturing cost lower. Fabrication can be done with standard microelectronics processes and materials, which allows low manufacturing cost in high volumes. The thin layered structure can have a high emissivity, up to 90%.

Because of the protecting or shielding layers, no additional encapsulation or package is necessarily needed.

In embodiments, the layered structure may include a single, optically semi-transparent thin metal layer.

The materials of the layers can be selected according to the thermal requirements. In order to be able to use the optical structure as an emitter, the structure must withstand the temperatures required in emitter use. Typically, in emitter applications temperatures of more than 400° C. are used, which the structure should preferably withstand unchanged for long periods of time. The operating temperature can also be higher, even more than 700° C. The emitter temperatures typically used may be in the range 400-1000° C. At the same time, the structure should maintain good optical matching. Stability means that the emissivity of the structure remains essentially unchanged at the desired wavelength range in the operating conditions of the structure for the duration of the operating lifetime of the structure.

The lossy semi-transparent metal layer may typically be manufactured from a metal, which has a high melting point, so that the device will withstand emitter use. To maintain the optical properties of the structure, the metal layer should remain unchanged at the operating temperature. In this connection, the term operating temperature refers to the temperature of the active area of the device. It should be stated in addition that the operating temperature of the device may deviate substantially from the ambient temperature, especially in emitter use.

Metals that are very suitable for manufacturing the semi-transparent layer include, for example, molybdenum and tungsten. Other materials, too, for example titanium, tantalum, platinum, niobium, or compounds thereof, can be used in some embodiments.

In the embodiments, the optical matching of the emission surface to the semi-transparent metal layer or layers may be achieved using a dielectric material layer of high refractive index or a stack of material layers with at least one dielectric layer having a high refractive index. The one optically-matching dielectric layer or layers is located between the semi-transparent metal layer and the emitting outer surface of the layered structure. The layered structure is thus matched optically to its environment, in such a way that the emissivity is brought to the desired level at the desired wavelength range. Typically, this wavelength radiation range is situated in the range of infrared radiation. The desired level can be, for example, quite low, or close to unity (1), i.e. close to 100% efficiency. The emissivity of the peak can be designed to be, for example, in the range 0.3-1. In most embodiments and applications it is also important that the emissivity remains stable as a function of time.

Materials suitable for optical matching layer or layers include, for example, silicon, silicon dioxide, silicon nitride, aluminium oxide or a combination of these.

Matching the parameters of the structure to a practical application can be made experimentally by seeking suitable materials and their optical thicknesses, so that the desired emissivity is achieved. For the matching, it is also possible to use computational methods and commercially available computer programs, with the aid of which values are calculated for the layer thicknesses to be used with the selected materials. After this, components can be manufactured, the properties of the components measured, and if necessary the final result can be improved iteratively. Optical wave impedance theory can be exploited in the calculation. The calculation of the optical properties of thin films is described, for example, in the book O. S. Heavens. Optical Properties of Thin Solid Films, Dover Publications Inc., New York, 1954. One skilled in the art can calculate values for suitable film thicknesses according to the principles presented in the present patent publication and by using the theory presented in the aforementioned literature reference (O. S. Heavens).

In embodiments, the dielectric layers may include shielding layers adapted to enclose the semi-transparent metal layer or layers to prevent chemical reactions with other layers of the layered structure as well as with ambient agents. The shielding layers are manufactured from a shielding material that withstands the temperatures required in emitter use, and that is able at these temperatures to protect the semi-transparent metal layer or layers from excessive oxidation, excessive mixing, or some other corresponding relatively rapidly affecting destructive mechanism. More specifically, the shielding material may comprise a chemically passive material, which does not react in the operating-temperature range with the semi-transparent metal layer. In addition, the material of the shielding layers is a material that can be relatively well penetrated by light in the desired wavelength range. In other words, a material that is optically lossless or slightly lossy in the desired wavelength range is chosen as the material. Thus, it is possible to improve the stability of the emissivity of the structure.

One very good material for a shielding material is silicon nitride. Silicon nitride works well as a passivation layer, i.e. water or oxygen cannot diffuse through the layer. Silicon nitride thus prevents the oxidation of the innermost layers even at high temperatures. Without a shielding layer, particularly thin metal films and metal conductors are easily damaged by oxidation. The metal atoms of the semi-transparent layer also do not diffuse through the silicon nitride. In addition, industrially applicable methods exist for depositing silicon nitride. With the aid of silicon nitride layers, it is possible to achieve operating temperatures of even more than 1000° C. Of course, the shielding layers can also be manufactured from some other material, which meets the corresponding or other requirements demanded by the application. If the operating temperature of the layered structure is designed to be lower, the range of available materials widens. Other materials, which can be considered at least in some embodiments of the layered structure, include, for example, aluminium oxide, aluminium nitride, silicon oxide, and silicon oxynitride.

In embodiments, the thickness of the semi-transparent metal layer or layers may be selected from a range 2 nm to 50 nm, preferably from a range 3 nm to 20 nm, more preferably from a range 5 nm to 15 nm.

In embodiments, the emissive area of the layered structure can be patterned, partly patterned or non-patterned. For example, a patterned emissive area may be obtained by a patterned optically-matching dielectric layer and/or a patterned semi-transparent metal layer. The area of the layered structure is more effectively used for infrared emission if it is kept non-patterned. On the other hand, with a patterned or partly patterned emissive area, an accurate geometry of the emissive area can be achieved. An accurate geometry allows use of imaging optics in Nondispersive Infrared (NDIR) applications.

The electric heating structure, such as heating resistor or wiring may be arranged in or between any one of the shielding dielectric layers. With the aid of a shielding material it is possible to protect the heating filament inside the structure. In embodiments, the electric heater structure may be optimized for uniform temperature distribution in the emissive area of the layered structure.

Figure 1B:
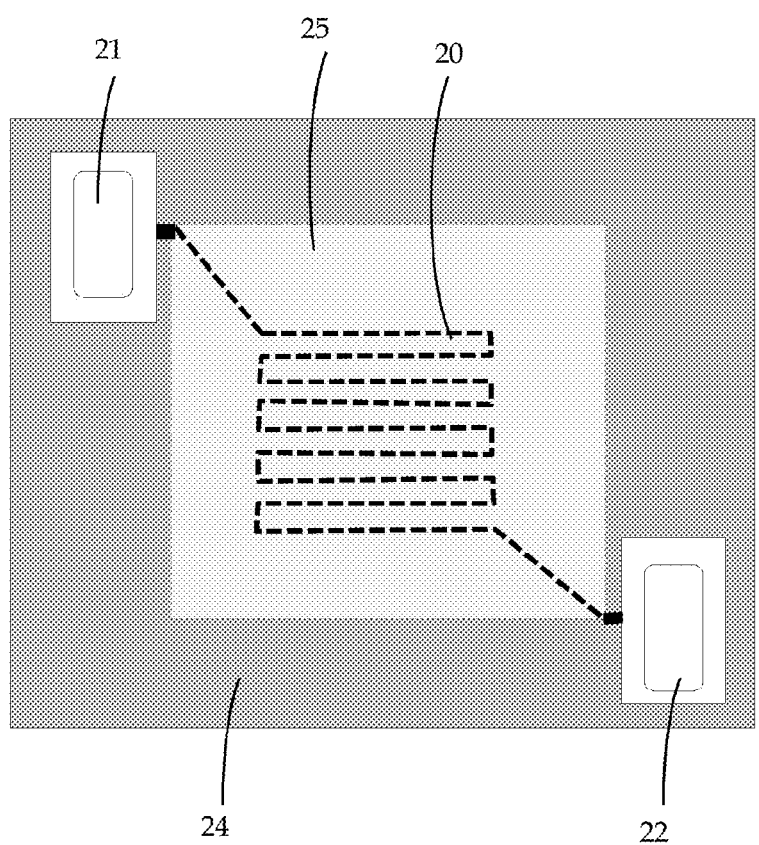
FIG. 1B shows a top view of the device shown in FIG. 1A.

A layered infrared emitter device according to an exemplary embodiment of the invention is schematically illustrated in cross-sectional side view in FIG. 1A and in top view in FIG. 1B. The exemplary layered infrared emitter structure may be manufactured on the top of a silicon substrate 24. The layered structure can be also manufactured on some other type of substrate, or without a separate substrate 24. The substrate 24 may have a central opening 25. The substrate 24 may then form a supporting frame under the layered structure. The substrate material 24 may for example be etched away at the location of the central opening 25.

The exemplary layered infrared emitter structure may contain a self-supporting dielectric shielding layer 17 on the top of the substrate 24. On top of the shielding layer 17 a second dielectric shielding layer 16, a semi-transparent metal layer 15 and a third dielectric shielding layer 14 may be provided. On the top of third dielectric shielding layer 14 there may be a fourth dielectric shielding layer 13 and an optically matching dielectric layer 12 having a high refractive index. On top of the optically matching dielectric layer 12 there may be a fifth shielding layer 11, the top surface of which may form an emissive surface 10 of the emitter device.

In the topmost shielding layer 11 there may be embedded a heating resistor wiring 20. Contact terminals 21 and 22 extending from the top surface to the heating resistor wiring 20 may be provided at the ends of the wiring 20 for supplying an electric heating current. The heating resistor 20 may alternatively be embedded into some other dielectric layer, such the dielectric shielding layer. In the example illustrated in FIG. 1B, the layout of heating resistor 20 is uniform, but alternatively the layout or pattern of the heating resistor may be tailored to provide a uniform temperature distribution in the emissive area of the layered structure. For example, the width and/or spacing of a resistor wiring 20 may vary as a function of a place along the emissive area.

The direction of the infrared emission from the emissive surface 10 is illustrated by the wide arrow. In the illustrated example the layered structure and the emissive surface are tailored for a front side operation. Alternatively, the layered structure and the emissive surface can be tailored for a back side operation for infrared emission through the central opening 25 in the substrate 24, for example. For the back side operation, the layers illustrated in the example structure of FIG. 1A may be arranged in a reversed order on the top of the substrate 24.

The materials and thickness of different layers in the exemplary layered structures illustrated in embodiments of FIGS. 1A and 1B may be selected as described above. An example of suitable materials and thicknesses is given in Table 1.

TABLE 1

| Layer | Material | Thickness |
| --- | --- | --- |
| 11 | $SI_3N_4$ | 100 nm |
| 12 | SIPOLY | 175 nm |
| 13 | $SI_3N_4$ | 30 nm |
| 14 | $Al_2O_3$ | 10 nm |
| 15 | Nb | 11 nm |
| 16 | $Al_2O_3$ | 10 nm |
| 17 | $SI_3N_4$ | 150 nm |

In the example shown in FIGS. 1A and 1B the emissive area of the layered infrared emitter structure is unpatterned.

Figure 2A:
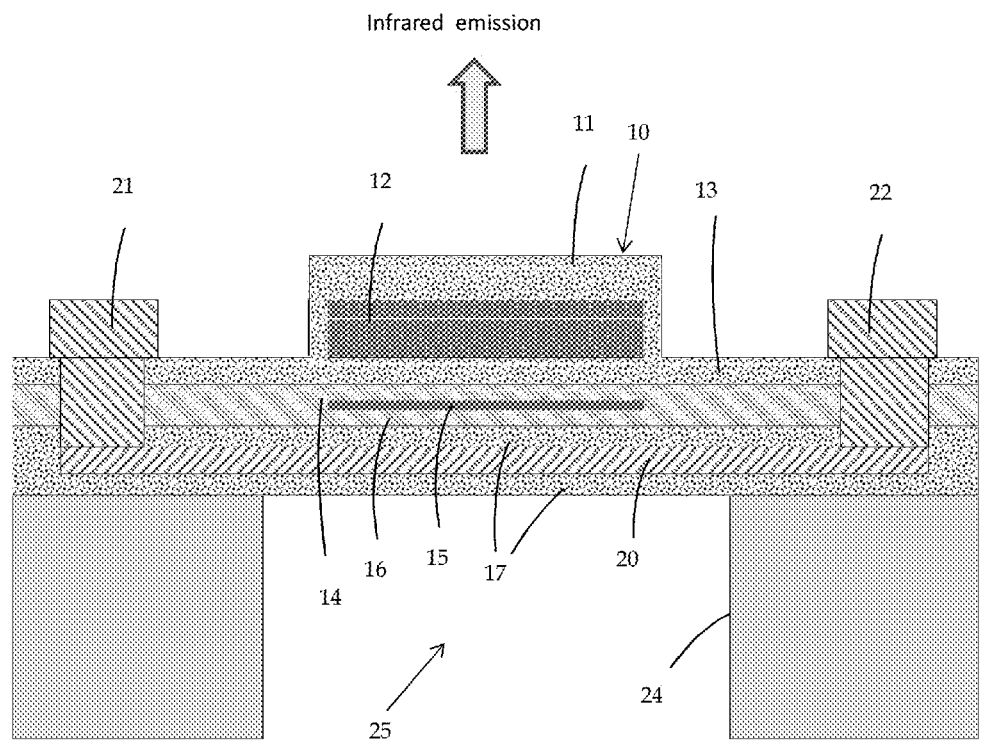
FIG. 2A shows a cross-sectional side view of a layered infrared emitter device according to an exemplary embodiment of the invention.
Figure 2B:
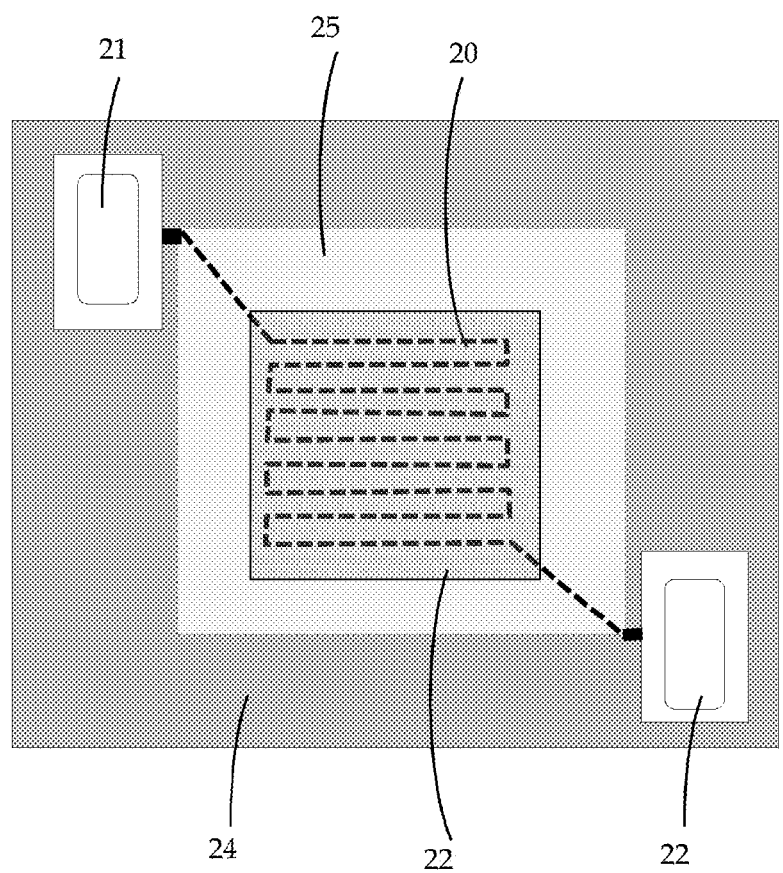
FIG. 2B shows a top view of the device shown in FIG. 2A.

A layered infrared emitter device according to another exemplary embodiment of the invention is schematically illustrated in cross-sectional side view in FIG. 2A and in top view in FIG. 2B. In the example shown in FIGS. 2A and 2B the emissive area of the layered infrared emitter structure is patterned, meaning that a geometrically defined portion of the entire area of the layered structure is used as the emissive area.

The exemplary layered infrared emitter structure may be manufactured on the top of a silicon substrate 24. The layered structure can be also manufactured on some other type of substrate, or without a separate substrate 24. The substrate 24 may have a central opening 25. The substrate 24 may then form a supporting frame under the layered structure. The substrate material 8 may for example be etched away at the location of the central opening 25.

The exemplary layered infrared emitter structure may contain a self-supporting dielectric shielding layer 17 on the top of the substrate 24. On top of the shielding layer 17 a second dielectric shielding layer 16 and a semi-transparent metal layer 15 may be provided. The semi-transparent metal layer 15 may be patterned so that it extends over a geometrically defined portion of the entire area of the dielectric shielding layer 16 and the layered structure.

On the top of the patterned semi-transparent metal layer 15 and the second dielectric shielding layer 16 there may be stacked a third dielectric shielding layer 13 and a fourth dielectric shielding layer 13. On the top of shielding layer 13 there may be an optically matching dielectric layer 12 having a high refractive coefficient. The optically matching dielectric layer 12 may be patterned so that it extends over a geometrically defined portion of the entire area of the dielectric shielding layer 13 and the layered structure. Thereby, the remaining portion of the shielding layer 13 may be left exposed to form an outer surface of the layered structure. Finally, the optically matching dielectric layer may be covered and enclosed by a fifth dielectric shielding layer 11, the top surface of which may form an emissive surface 10 of the emitter device.

In the bottom most shielding layer 17 there may be embedded a heating resistor wiring 20. Contact terminals 21 and 22 that extend from the top surface of the shielding layer 13 through the shielding layers 13 and 16 to the heating resistor wiring 20 in the shielding layer 17 may be provided at the ends of the wiring 20 for supplying an electric heating current. The heating resistor 20 may alternatively be embedded into some other dielectric layer. In the example illustrated in FIG. 2B, the layout of heating resistor 20 is uniform, but it may alternatively be tailored to provide a uniform temperature distribution.

In the illustrated example the layered structure and the emissive surface are tailored for a front side operation. Alternatively, the layered structure and the emissive surface can be tailored for a back side operation for infrared emission through the central opening 25 in the substrate 24, for example. For the back side operation, the layers illustrated in the example structure of FIG. 2A may be arranged in a reversed order on the top of the substrate 24.

The materials and thickness of different layers in the exemplary layered structures illustrated in embodiments of FIGS. 2A and 2B may be selected as described above. An example of suitable materials and thicknesses is given in Table 2.

TABLE 2

| Layer | Material | Thickness |
| --- | --- | --- |
| 11 | $SI_3N_4$ | 100 nm |
| 12 | SIPOLY | 175 nm |
| 13 | $SI_3N_4$ | 30 nm |
| 14 | $Al_2O_3$ | 10 nm |
| 15 | Nb | 11 nm |
| 16 | $Al_2O_3$ | 10 nm |
| 17 | $SI_3N_4$ | 150 nm |

Figure 3:
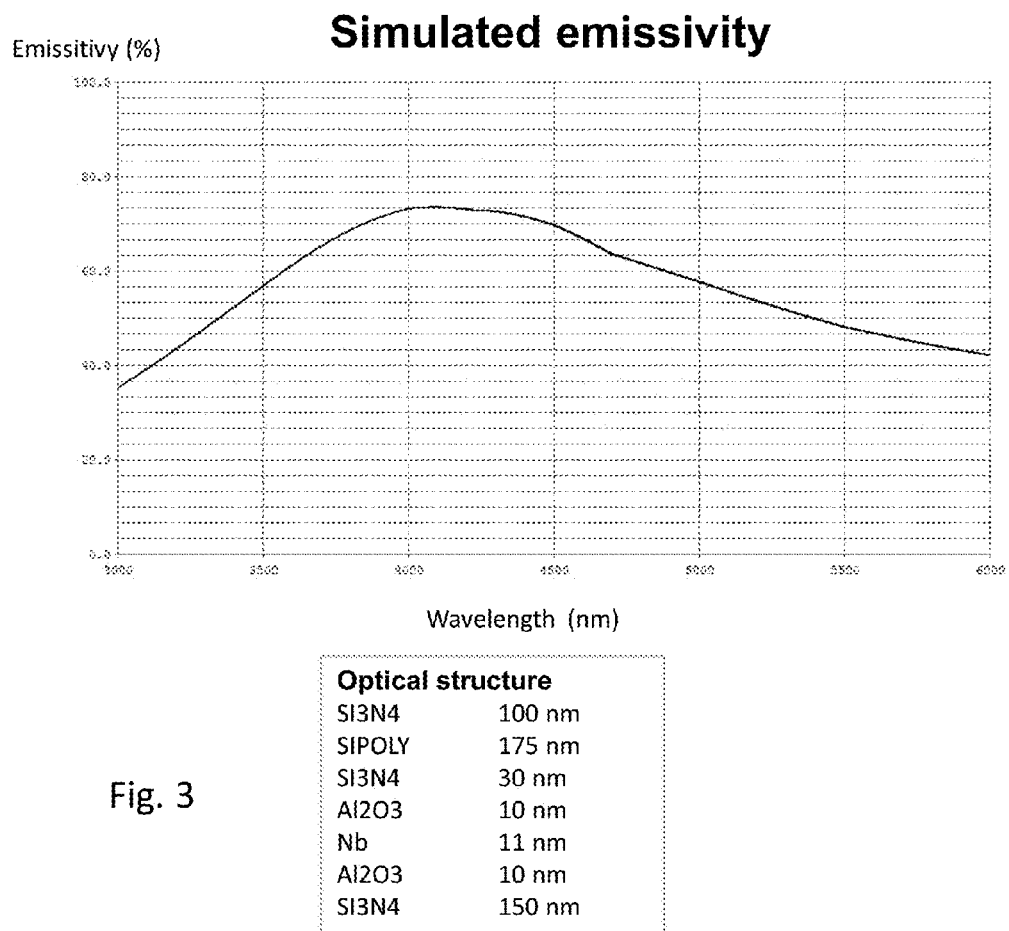
FIG. 3 shows an example of a simulated emissivity as a function of wavelength.

FIG. 3 shows an example of a simulated emissivity as a function of wavelength for a layered infrared emitter structure with the exemplary parameters given in Table 1 or 2.

Figure 4:
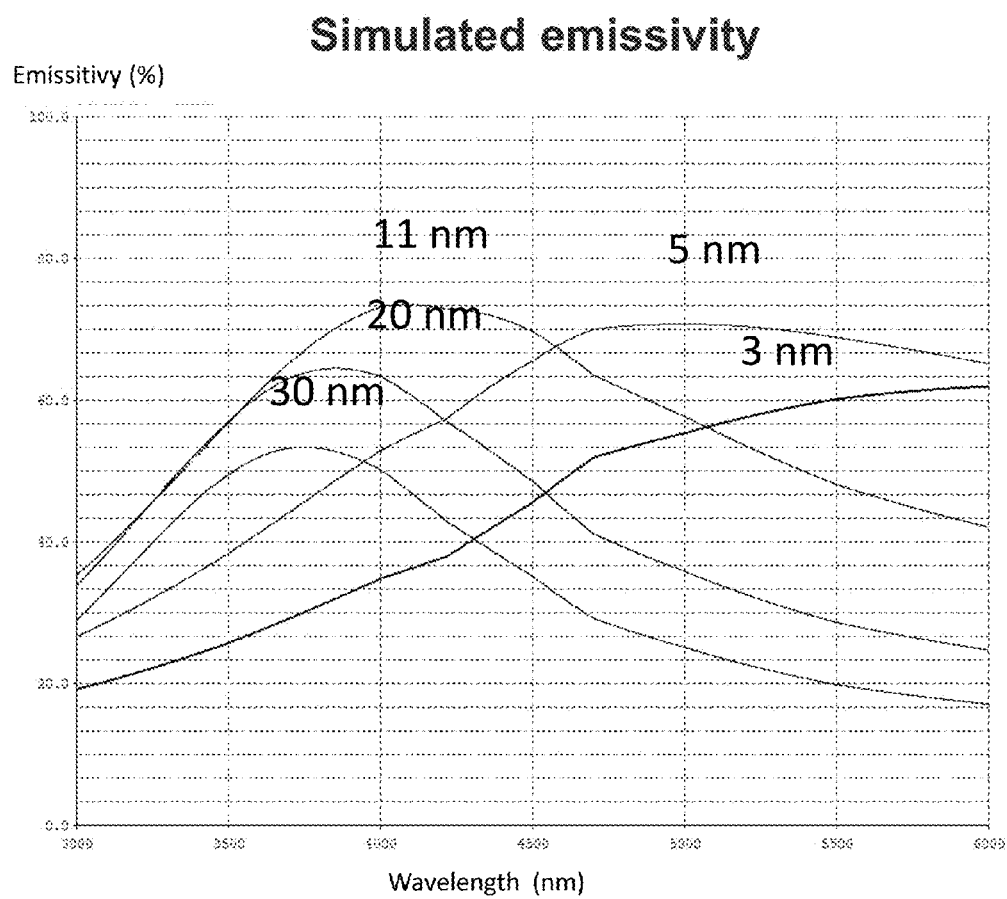
FIG. 4 shows an example of the effect of the thickness of the semi-transparent Nb layer on a simulated emissivity as a function of wavelength.

FIG. 4 shows an example of the effect of the thickness of the semi-transparent Nb layer on a simulated emissivity as a function of wavelength for a layered infrared emitter structure. Other parameter values are the same as in FIG. 3.

The layered infrared emitter device is particularly suitable for spectroscopic and NDIR gas, liquid and solid matter measurement applications.

The invention and its embodiments are not limited to the examples den scribed above but may vary within the scope of the claims.

The invention claimed is:

1. A layered infrared emitter device, which comprises a layered structure having at least one metal layer stacked between two or more dielectric layers, and an electric heating means arranged in or between any of the dielectric layers to heat the at least one metal layer to a required infrared emission temperature, preferably to a temperature within a range from 400° C. to 1000° C., wherein each metal layer in the layered structure is a semi-transparent metal layer.

2. The layered infrared emitter device as claimed in claim 1, wherein the layered structure comprises only one metal layer.

3. The layered infrared emitter device as claimed in claim 1, wherein the layered structure comprises a stack of semi-transparent metal layers.

4. The infrared emitter device as claimed in claim 1, wherein the thickness of the semi-transparent metal layer is selected from a range 2 nm to 50 nm, preferably from a range 3 nm to 20 nm, more preferably from a range 5 nm to 15 nm.

5. The infrared emitter device as claimed in claim 1, wherein the semi-transparent metal layer is made of a thermally stable metal, the metal being preferably selected from preferably selected from refractory or noble metals, more preferably from the group of such as molybdenum, tungsten, titanium, tantalum, palladium, platinum or niobium.

6. The layered infrared emitter device as claimed in claim 1, wherein at least one of the dielectric layers is adapted to optically match the at least one semi-transparent metal layer to an emitting outer surface of the layered structure, and wherein the at least one optically-matching dielectric layer is being preferably made of polysilicon material or other dielectric material having a high refractive index.

7. The infrared emitter device as claimed in claim 6, wherein the thickness of the at least one optically-matching dielectric layer is several times larger than the thickness of the at least one semi-transparent metal layer.

8. The infrared emitter device as claimed in claim 6, wherein the at least one optically-matching dielectric layer and/or the at least one semi-transparent metal layer is patterned, partly patterned.

9. The infrared emitter device as claimed in claim 1, wherein the dielectric layers include shielding layers adapted to enclose the at least one semi-transparent layer to prevent chemical reactions with other layers of the layered structure as well as with ambient agents.

10. The infrared emitter device as claimed in claim 1, wherein the dielectric layers include shielding layers adapted to prevent chemical reactions between different layers of the layered structure as well as with ambient agents, at least one of the shielding layers being preferably made of material selected from a group of silicon nitrate, polycrystalline, and metal oxides, such as aluminium oxide.

11. The infrared emitter device as claimed in claim 1, wherein the layered structure comprises in order from an emitting side to an opposite side,
at least one shielding dielectric layer,
an optically-matching dielectric layer having a high refractive index,
at least one shielding dielectric layer,
the semi-transparent metal layer,
at least one shielding dielectric layer,
and wherein the electric heating means is arranged in or between of the shielding dielectric layers.

12. The infrared emitter device as claimed in claim 1, wherein the layered structure comprises in order from an emitting side to an opposite side a first shielding dielectric layer,
an optically-matching dielectric layer having a high refractive index,
a second shielding dielectric layer,
a third shielding dielectric layer,
the semi-transparent metal layer which is the only metal layer in the layered structure,
a fourth shielding dielectric layer, and
a fifth shielding dielectric layer, and
the electric heating means being arranged in or between any one of the shielding dielectric layers.

13. Use of an infrared emitter device for spectroscopic or NDIR gas, liquid or solid matter measurement, the infrared emitter device comprising a layered structure having at least one metal layer stacked between two or more dielectric layers, and an electric heating means arranged in or between any of the dielectric layers to heat the at least one metal layer to a required infrared emission temperature, preferably to a temperature within a range from 400° C. to 1000° C., wherein each metal layer in the layered structure is a semi-transparent metal layer.

* * * * *